(12) United States Patent
Cheung

(10) Patent No.: US 7,778,531 B2
(45) Date of Patent: Aug. 17, 2010

(54) DISPOSABLE AIR FRESHENER CONFIGURED FOR CONNECTION TO USB PORT

(76) Inventor: David Cheung, Flat C, 20/F, Gold King Building, 35-41 Tai Lin Pai Road, Kwai Chung, Hong Kong (CN)

( * ) Notice: Subject to any disclaimer, the term of this patent is extended or adjusted under 35 U.S.C. 154(b) by 202 days.

(21) Appl. No.: 12/013,083

(22) Filed: Jan. 11, 2008

(65) Prior Publication Data

US 2008/0179424 A1    Jul. 31, 2008

Related U.S. Application Data

(60) Provisional application No. 60/897,592, filed on Jan. 26, 2007.

(51) Int. Cl.
*A01G 13/06* (2006.01)
(52) U.S. Cl. ...................... 392/386; 392/390
(58) Field of Classification Search ............... None
See application file for complete search history.

(56) References Cited

U.S. PATENT DOCUMENTS

| | | | | |
|---|---|---|---|---|
| 5,876,678 A * | 3/1999 | Harrell et al. | ............... | 422/125 |
| 5,945,094 A * | 8/1999 | Martin et al. | ............... | 424/76.1 |
| 5,976,503 A * | 11/1999 | Martin et al. | ............... | 424/43 |
| 6,123,935 A * | 9/2000 | Wefler et al. | ............... | 424/76.1 |
| 6,168,088 B1 * | 1/2001 | Mobley | ............... | 239/6 |
| 6,609,935 B2 * | 8/2003 | Huang | ............... | 439/620.16 |
| 6,631,852 B1 * | 10/2003 | O'Leary | ............... | 239/60 |
| 2009/0148142 A1 * | 6/2009 | McGee et al. | ............... | 392/387 |

* cited by examiner

*Primary Examiner*—Thor S Campbell
(74) *Attorney, Agent, or Firm*—Raymond Nuzzo

(57) ABSTRACT

A disposable air freshener configured to be connected to a USB port of a computer or computer peripheral device. In one embodiment, the disposable air freshener comprises a casing fabricated from a plurality of sections that have generally the same shape. At least one of these sections is configured as scented cardboard. The disposable air freshener has a printed circuit board and a heating element electrically connected to the printed circuit board. A portion of the printed circuit board extends from the casing and is configured to be inserted into a USB port so that electrical power can be applied to the printed circuit board. The heating element generates heat when it receives electrical power from the printed circuit board. Thus, when electrical power is applied to the printed circuit board, the heating element generates heat which causes the scented cardboard to emit a pleasant scent or aroma. The casing of the air freshener can be configured to have almost any geometric shape, e.g. pine tree, hamburger, chocolate bar, etc.

14 Claims, 9 Drawing Sheets

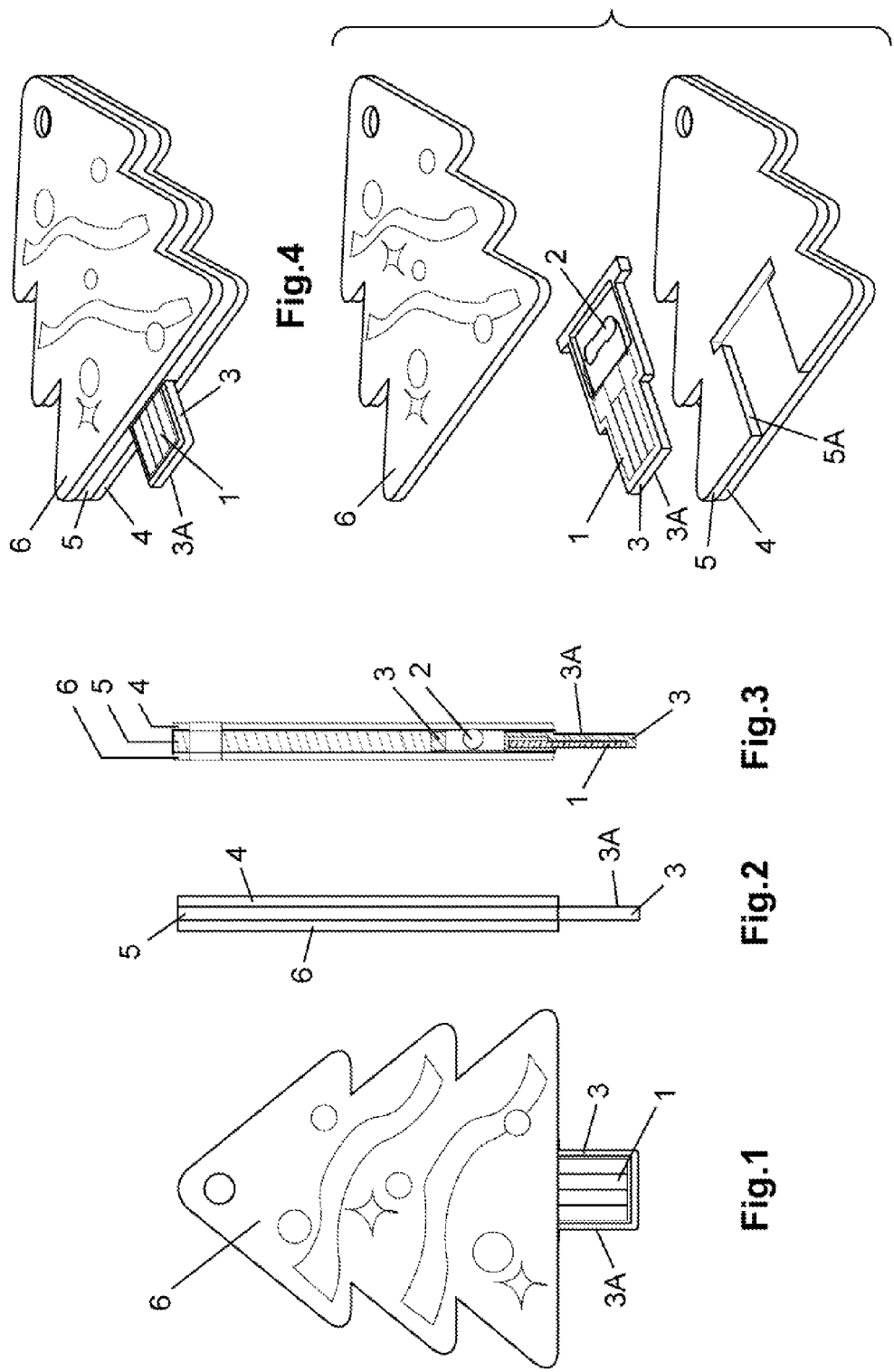

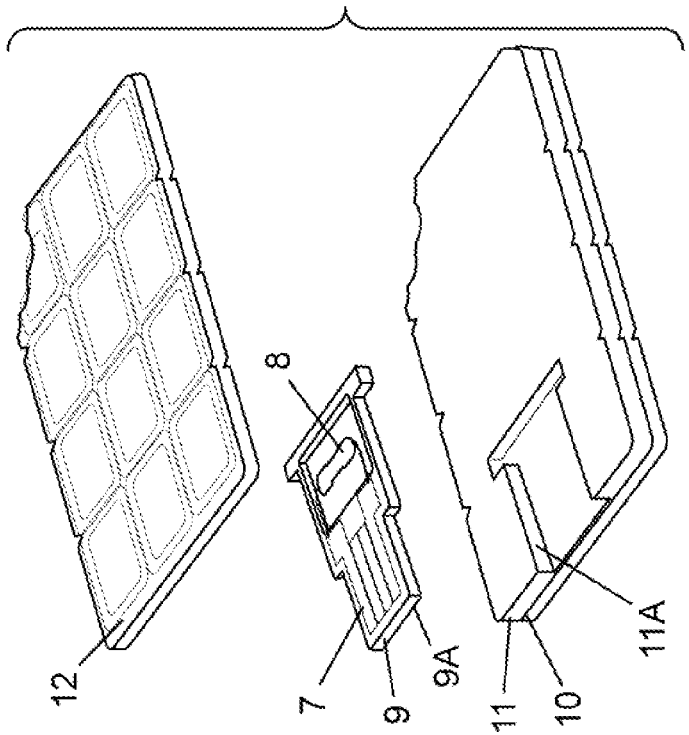
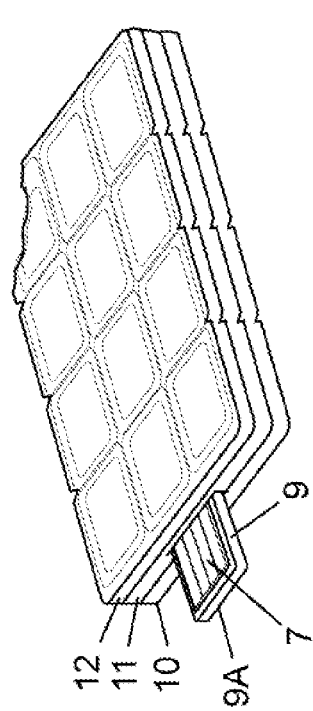
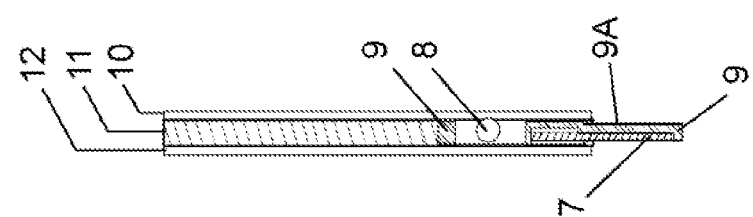
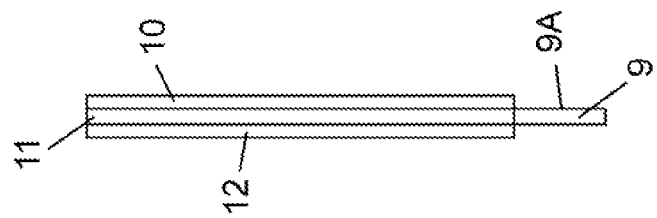
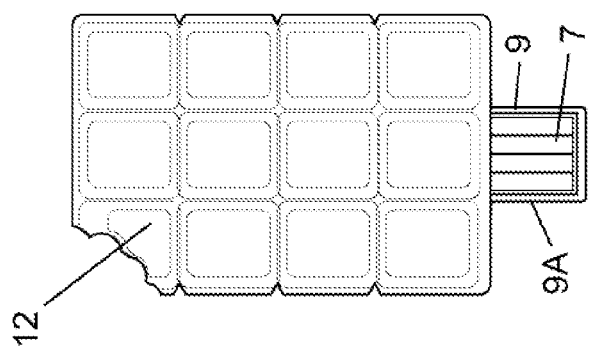

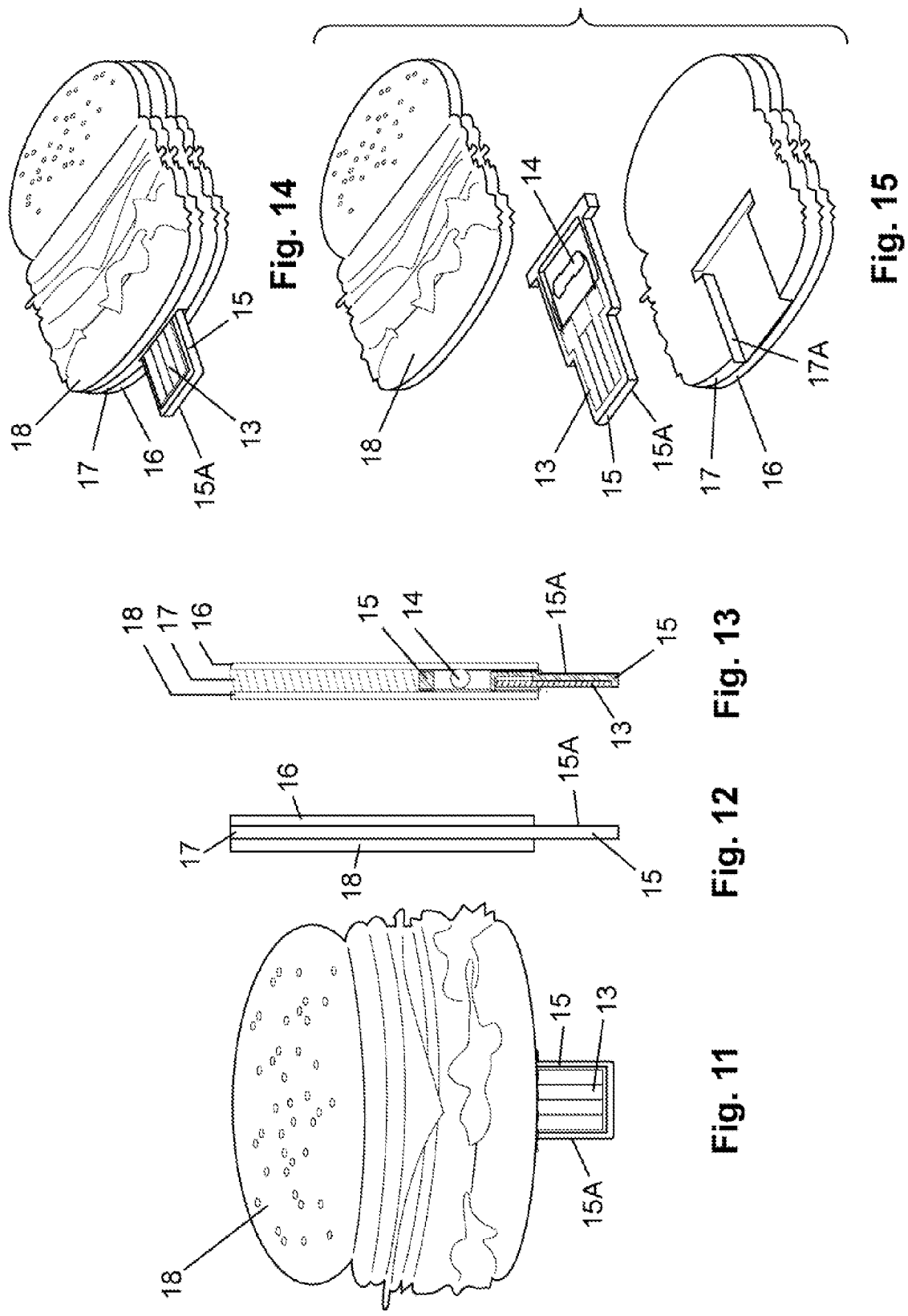

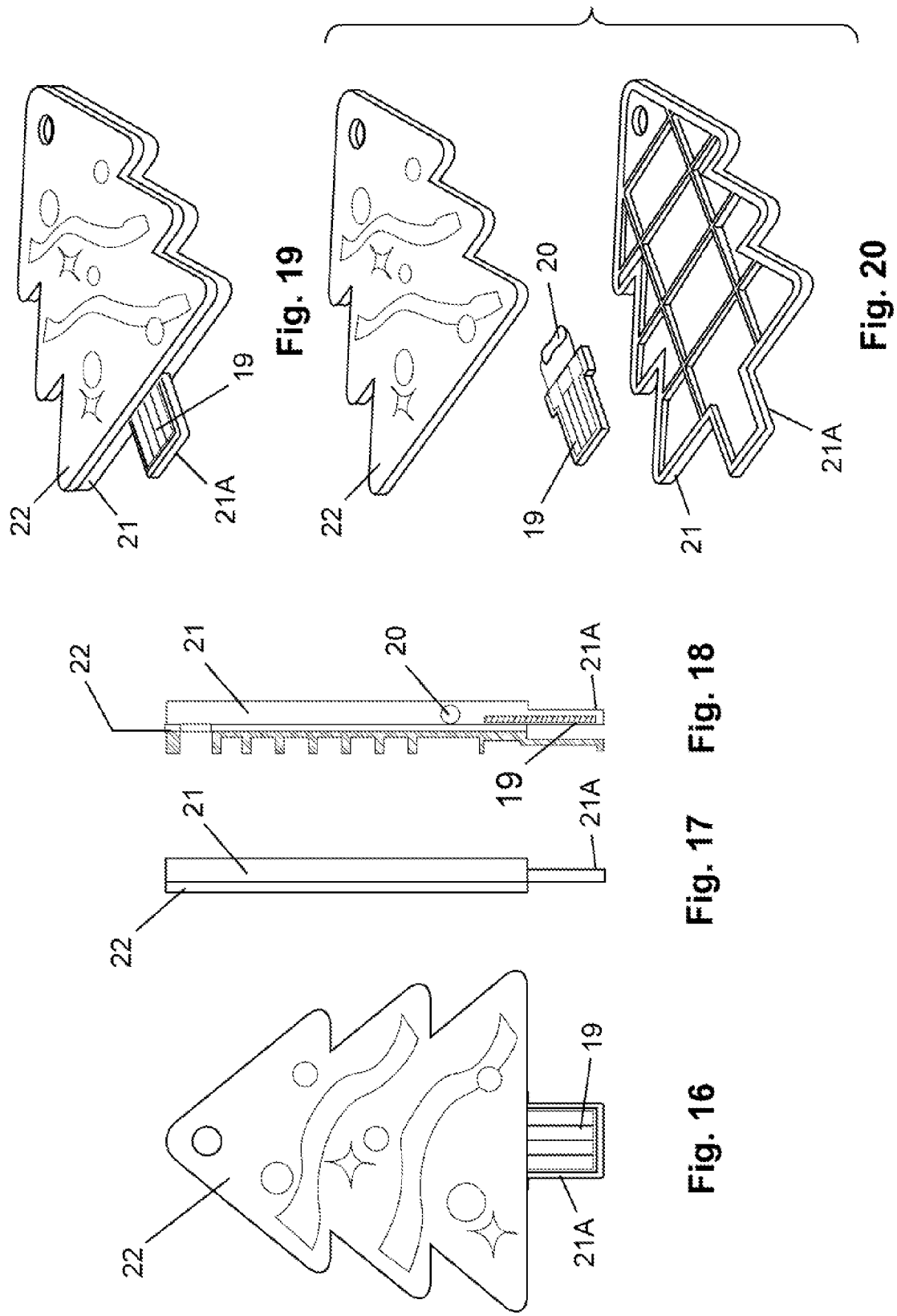

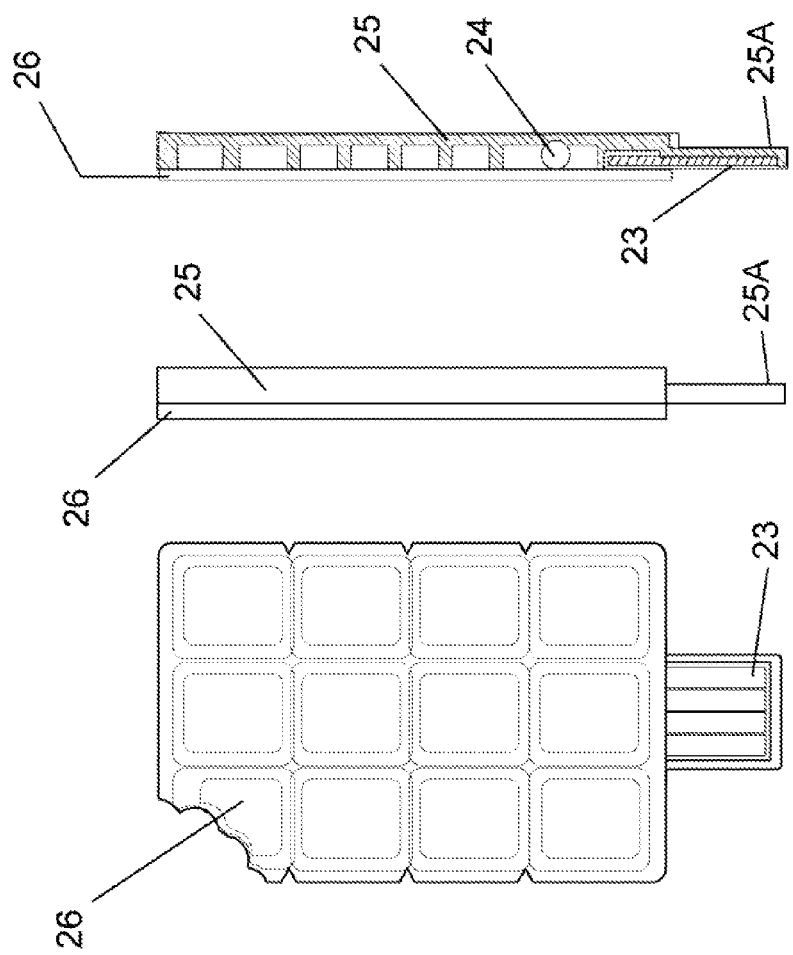

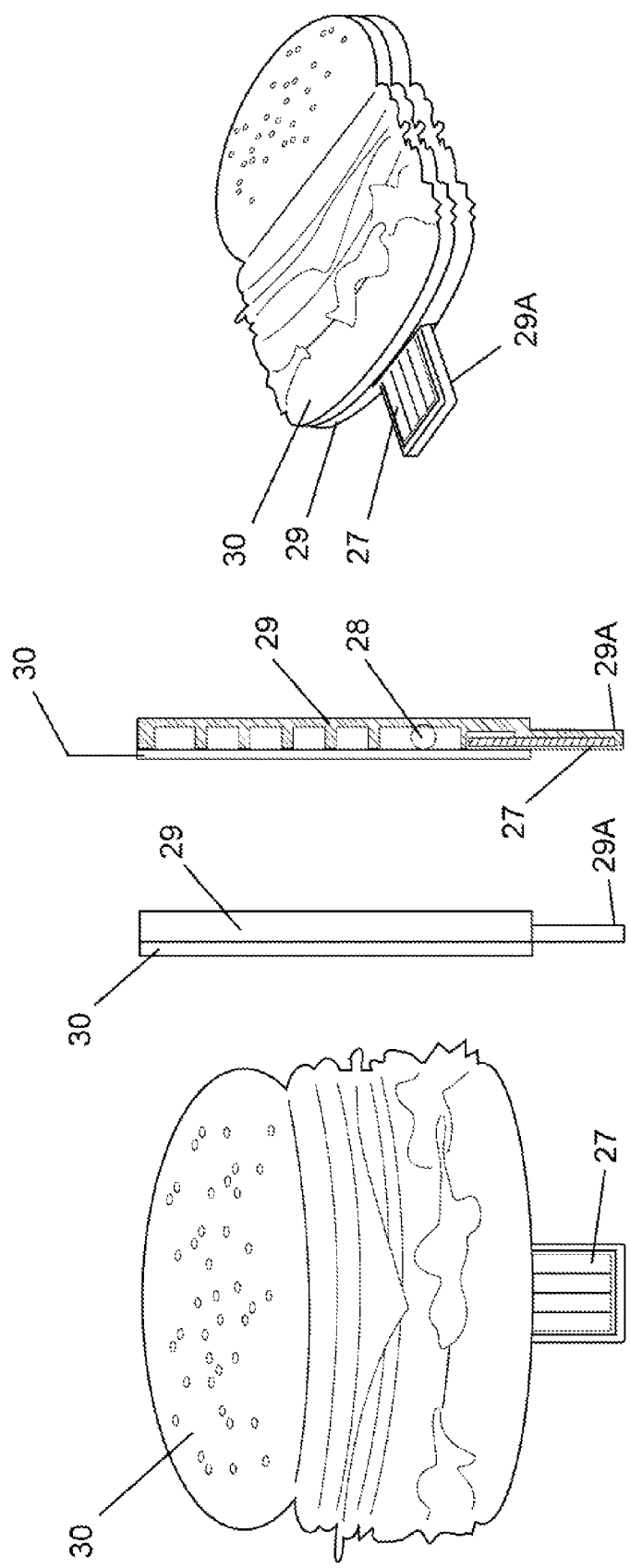

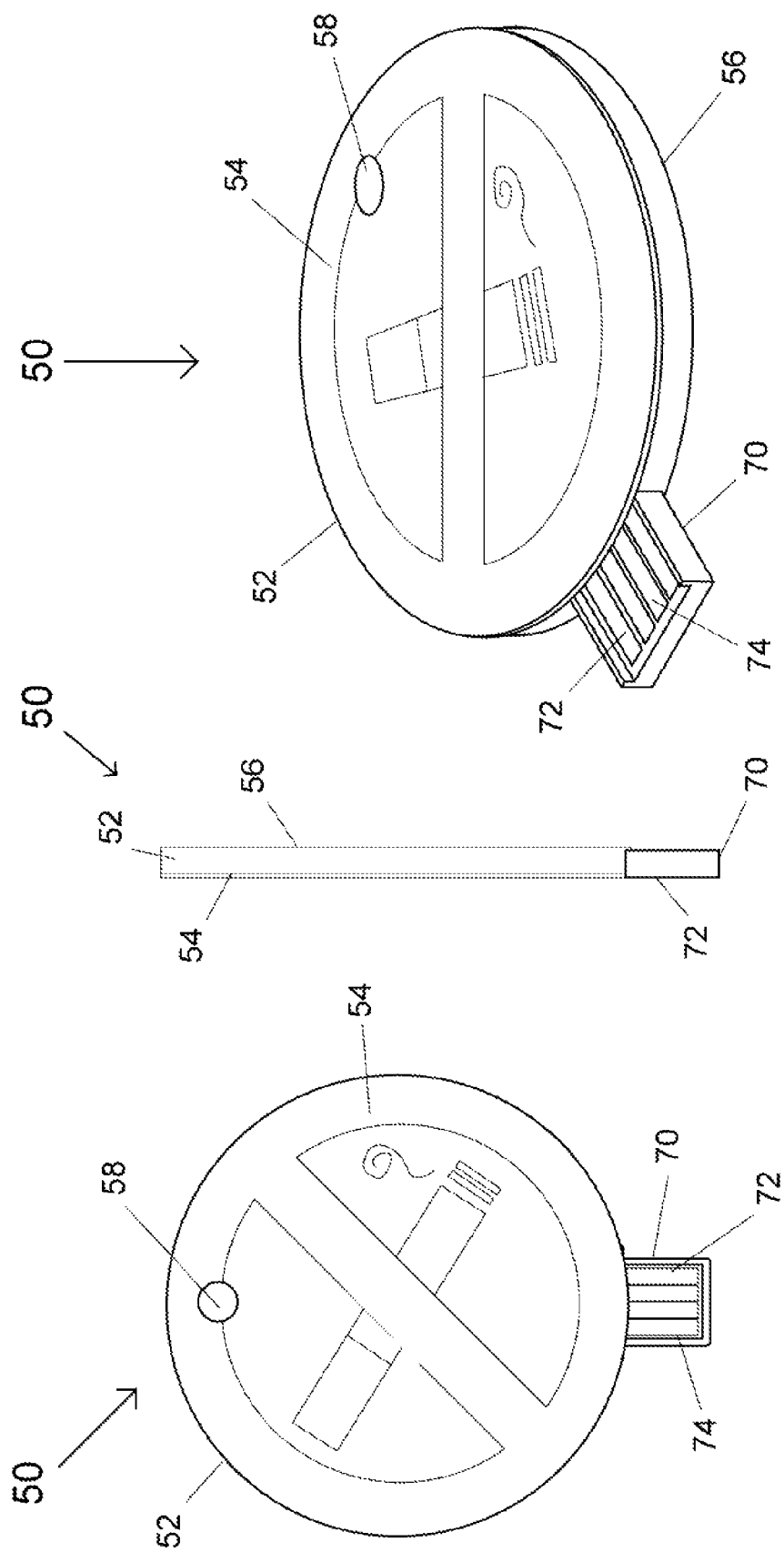

DISPOSABLE AIR FRESHENER CONFIGURED FOR CONNECTION TO USB PORT

CROSS-REFERENCE TO RELATED APPLICATIONS

This application claims the benefit of U.S. Provisional Application No. 60/897,592, filed Jan. 26, 2007. Application No. 60/897,592 is hereby incorporated by reference.

BACKGROUND OF THE INVENTION

1. Field of the Invention

The present invention generally relates to an air freshener that is configured to be connected to and powered by a USB port.

2. Description of Related Art

USB ports are widely used in the computer field and are used to connect computer peripheral devices together or to a computer. Low level electrical power is typically available at a USB port.

SUMMARY OF THE INVENTION

The present invention is directed to a disposable air freshener that can be plugged into a USB port of a computer or computer peripheral device. The disposable air freshener comprises a casing fabricated from a plurality of sections that have generally the same shape. At least one of these sections is configured as scented cardboard. The disposable air freshener further comprises a printed circuit board and a heating element electrically connected to the printed circuit board. When electrical power is applied to the heating element, the heating element generates heat. A portion of the printed circuit board extends from the casing and is configured to be plugged into a USB port so that electrical power can be applied to the printed circuit board. The heating element generates heat when it receives electrical power from the printed circuit board. This heat causes the scented cardboard to emit a pleasant scent or aroma. The casing of the air freshener can be configured to any one of a variety of geometric shapes, e.g. tree, hamburger, chocolate bar, etc. The casing may have a geometric shape that matches the shape of other consumer objects as well.

Other embodiments of the disposable air freshener of the present invention are also described herein.

BRIEF DESCRIPTION OF THE DRAWINGS

The foregoing features of the present invention will become more readily apparent and may be understood by referring to the following detailed description of an illustrative embodiment of the present invention, taken in conjunction with the accompanying drawings, in which:

FIG. 1 is front view of an air freshener in accordance with one embodiment of the present invention, the rear side being generally the same;

FIG. 2 is a side view, in elevation, of the air freshener of FIG. 1;

FIG. 3 is a view, partially in cross-section, of the air freshener of FIG. 1;

FIG. 4 is a perspective view of the air freshener of FIG. 1;

FIG. 5 is an exploded view of the air freshener of FIG. 1;

FIG. 6 is front view of an air freshener in accordance with another embodiment of the present invention;

FIG. 7 is a side view, in elevation, of the air freshener of FIG. 6;

FIG. 8 is a view, partially in cross-section, of the air freshener of FIG. 6;

FIG. 9 is a perspective view of the air freshener of FIG. 6;

FIG. 10 is an exploded view of the air freshener of FIG. 6;

FIG. 11 is front view of an air freshener in accordance with a further embodiment of the present invention;

FIG. 12 is a side view, in elevation, of the air freshener of FIG. 11;

FIG. 13 is a view, partially in cross-section, of the air freshener of FIG. 11;

FIG. 14 is a perspective view of the air freshener of FIG. 11;

FIG. 15 is an exploded view of the air freshener of FIG. 11;

FIG. 16 is front view of an air freshener in accordance with a further embodiment of the present invention;

FIG. 17 is a side view, in elevation, of the air freshener of FIG. 16;

FIG. 18 is a view, partially in cross-section, of the air freshener of FIG. 16;

FIG. 19 is a perspective view of the air freshener of FIG. 16;

FIG. 20 is an exploded view of the air freshener of FIG. 16;

FIG. 21 is front view of an air freshener in accordance with a further embodiment of the present invention, the rear side being generally the same;

FIG. 22 is a side view, in elevation, of the air freshener of FIG. 21;

FIG. 23 is a view, partially in cross-section, of the air freshener of FIG. 21;

FIG. 25 is a front view of an air freshener in accordance with another embodiment of the present invention, the rear side being generally the same;

FIG. 26 is a side view, in elevation, of the air freshener of FIG. 25;

FIG. 27 is view, partially in cross-section, of the air freshener of FIG. 25;

FIG. 28 is a perspective view of the air freshener of FIG. 25;

FIG. 29 is a top plan view of an air freshener in accordance with a further embodiment of the present invention;

FIG. 30 is a side view of the air freshener shown in FIG. 29;

FIG. 31 is a perspective view of the air freshener shown in FIG. 29; and

DESCRIPTION OF THE PREFERRED EMBODIMENTS

Figure 24:
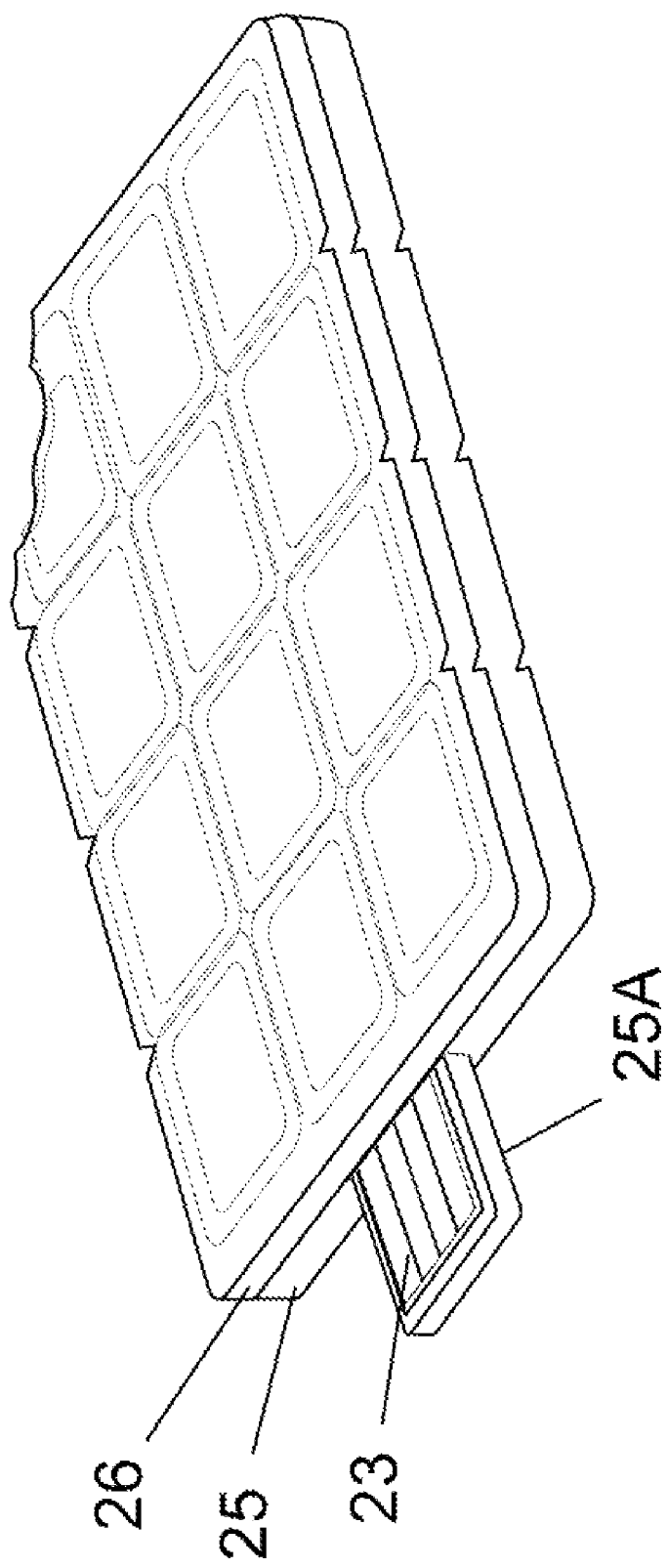
FIG. 24 is a perspective view of the air freshener of FIG. 21.
Figure 32:
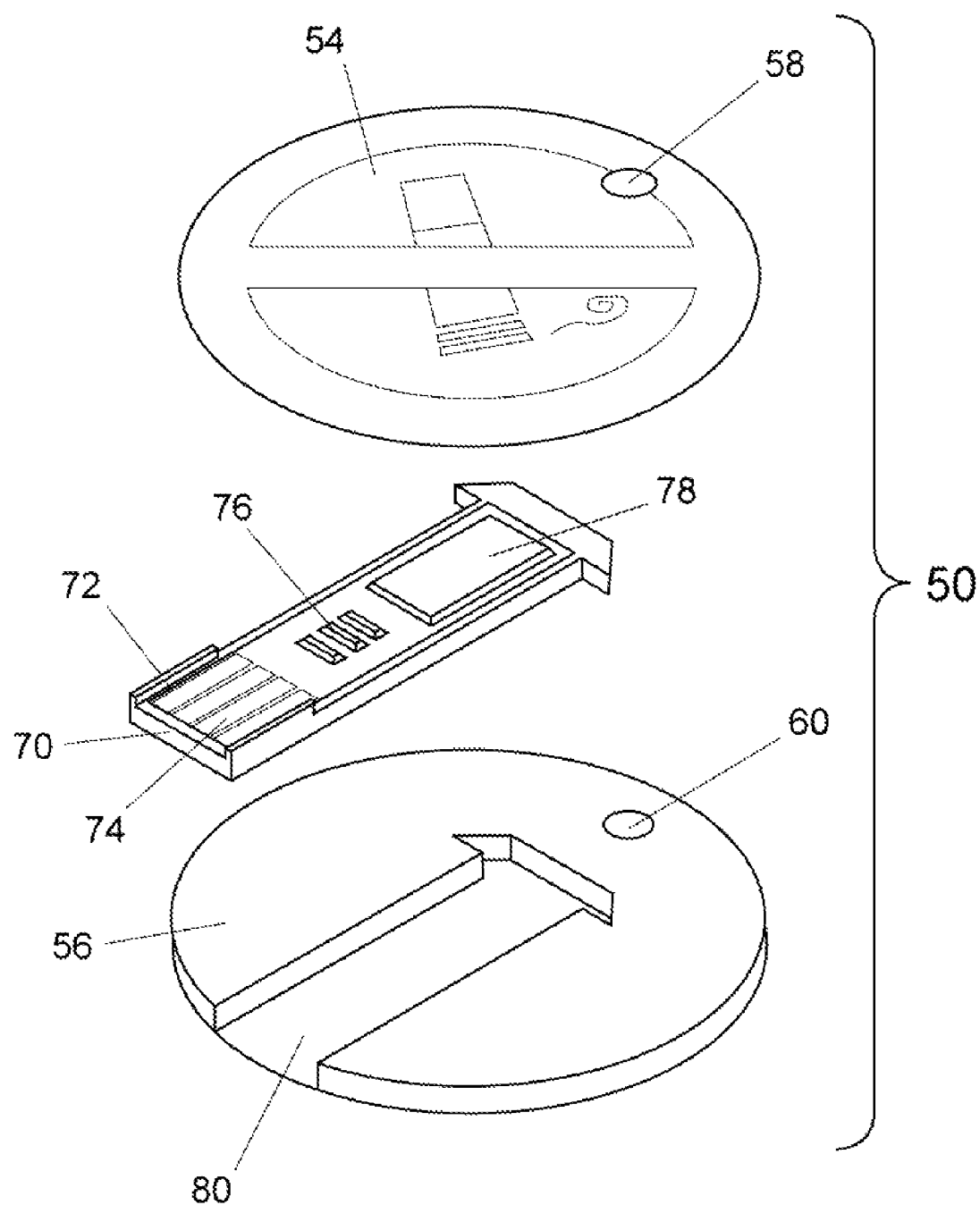
FIG. 32 is an exploded view of the air freshener shown in FIG. 29.

Referring to FIGS. 1-5, there is shown an air freshener in accordance with one embodiment of the present invention. In a preferred embodiment, this air freshener is disposable. The air freshener comprises a casing that is formed of cardboard and has sections 4, 5 and section 6. Cardboard sections 4, 5 and 6 are configured as scent-absorbing cardboard. When heat is applied to the cardboard sections, the cardboard sections emit a scent or fragrance. Sections 4, 5 and 6 have the shape of a pine tree. Section 5 is sandwiched between sections 4 and 6. The air freshener comprises a USB connector structure 3 that comprises portion 3A which is inserted into a USB port of a computer or computer peripheral device. Printed circuit board 1 is also part of USB connector structure 3. Heating element 2 is joined to a printed circuit board 1. Heating element 2 can be configured as any suitable electronic component that can generate heat when electrical power is applied to it. In a preferred embodiment, heating element 2 is a resistor. Section 5 of the casing has a cut-out 5A that has a shape that conforms to the shape of USB connector structure 3. Thus, USB connector structure 3 fits into cut-out 5A. As a result of this configuration, USB connector structure 3 is firmly and neatly sandwiched between casing sections 4 and 6. In one embodiment, sections 4, 5 and 6 can be laminated into a single structure. When portion 3A of USB connector structure 3 is plugged into a USB port of a computer or peripheral device, electrical power is applied to printed circuit board 1 and hence, to heating element 2. As a result, heating element 2 generates heat which causes the scented cardboard sections 4, 5 and 6 to emit a scent or fragrance. The cardboard sections 4 and 6 can be configured with designs and artwork which can be printed on the cardboard sections. Cardboard sections 4, 5 and 6 can be configured to have any one of a variety of scents using any one of a variety of known suitable techniques, and such scents or aromas include perfumes, herbs, fruit, flowers, etc. In one embodiment, the fragrance or scent is applied to the cardboard by printing, including offset printing, block printing, and screen printing. These printing techniques are known in the art.

Referring to FIGS. 6-10, there is shown an air freshener in accordance with another embodiment of the present invention. In a preferred embodiment, this air freshener is disposable. This air freshener comprises a casing that is formed of scent-absorbing cardboard and has cardboard sections 10, 11 and section 12. Each cardboard section 10, 11 and 12 is configured as scent-absorbing cardboard. In this embodiment, sections 10, 11 and 12 have the shape of a chocolate bar. Section 11 is sandwiched between sections 10 and 12. The air freshener comprises a USB connector structure 9 that comprises portion 9A which is inserted into a USB port of a computer or computer peripheral device. Printed circuit board 7 is also part of USB connector structure 9. Heating element 8 is electrically connected to printed circuit board 7. Heating element 8 can be configured as any suitable electronic component that can generate heat when electrical power is applied to it. In one embodiment, heating element 8 is a resistor. Section 11 of the casing has a cut-out 11A that has a shape that conforms to the shape of USB connector structure 9. Thus, USB connector structure 9 fits into cut-out 11A. As a result of this configuration, USB structure 9 is firmly and neatly sandwiched between casing sections 10 and 12. Sections 10, 11 and 12 can be laminated into a single structure. When portion 9A of USB connector structure 9 is plugged into a USB port of a computer or peripheral device, electrical power is applied to the printed circuit board 7 and thus, to heating element 8. In response to this electrical power, heating element 8 generates heat that causes cardboard sections 10, 11 and 12 to emit a scent or fragrance. Cardboard sections 10, 11 and 12 can be configured to have any one of a variety of scents or aromas using known techniques, and such scents or aromas include perfumes, herbs, fruit, flowers, etc. In one embodiment, the fragrance or scent is applied to the cardboard by printing, including offset printing, block printing, and screen printing. These printing techniques are known in the art.

Referring to FIGS. 11-15, there is shown an air freshener in accordance with a further embodiment of the present invention. In a preferred embodiment, this air freshener is disposable. The air freshener comprises a casing that is formed of cardboard and has sections 16, 17 and 18. Cardboard sections 16, 17 and 18 are configured as scent-absorbing cardboard. In this embodiment, sections 16, 17 and 18 have the shape of a hamburger. Section 17 is sandwiched between sections 16 and 18. The air freshener comprises a USB connector structure 15 that comprises portion 15A which is inserted into a USB port of a computer or computer peripheral device. Printed circuit board 13 is also part of USB connector structure 15. Heating element 14 is electrically connected to printed circuit board 13. Heating element 14 can be configured as any suitable electronic component that can generate heat when electrical power is applied to it. In a preferred embodiment, heating element 14 is a resistor. Section 17 of the casing has a cut-out 17A that has a shape that conforms to the shape of USB connector structure 15. Thus, USB connector structure 15 fits into cut-out 17A. As a result of this configuration, USB structure 15 is firmly and neatly sandwiched between casing sections 16 and 18. In one embodiment, sections 16, 17 and 18 can be laminated into a single structure. When portion 15A of USB connector structure 15 is plugged into a USB port of a computer or peripheral device, electrical power is applied to printed circuit board and to heating element 14. In response, heating element 14 generates heat that causes the scent-absorbing cardboard sections 16, 17 and 18 to emit a scent or fragrance. The cardboard sections 16, 17 and 18 can be configured to have any one of a variety of scents or aromas including perfumes, herbs, fruit, flowers, etc. In one embodiment, the fragrance or scent is applied to the cardboard by printing, including offset printing, block printing, and screen printing. These printing techniques are known in the art.

Referring to FIGS. 16-20, there is shown an air freshener in accordance with another embodiment of the present invention. In a preferred embodiment, this air freshener is disposable. This air freshener comprises a casing that is formed of sections 21 and 22. Section 22 is fabricated from scent-absorbing cardboard. Section 21 is configured as a hard structure, such as plastic, wood, etc. Section 21 is formed into the same shape as cardboard section 22. In this embodiment, sections 21 and 22 have the shape of a pine tree. Section 21 has extending portion 21A. Portion 21A is shaped so that it can be inserted into a USB port. Printed circuit board 19 is connected to portion 21A. A portion of printed circuit board 19 is exposed so that it can electrically contact corresponding electrical contacts in a USB port. A heating element 20 is electrically connected to printed circuit board 19. Heating element 20 can be configured as any suitable electronic component that can generate heat when electrical power is applied to it. In a preferred embodiment, heating element 20 is a resistor. Printed circuit board 19 and heating element 20 are sandwiched within casing sections 21 and 22. In one embodiment, cardboard section 22 is glued to section 21. When portion 21A of casing 21 is plugged into a USB port of a computer or peripheral device, electrical power is applied to printed circuit board 19. This electrical power is applied to heating element 20. As a result, heating element 20 generates heat that causes cardboard section 22 to emit a scent or fragrance. Cardboard section 22 can be configured to have any one of a variety of scents or aromas, including perfumes, herbs, fruit, flowers, etc. In one embodiment, the fragrance or scent is applied to the cardboard by printing, including offset printing, block printing, and screen printing. These printing techniques are known in the art.

Referring to FIGS. 21 and 24, there is shown an air freshener in accordance with a further embodiment of the present invention. In a preferred embodiment, this air freshener is disposable. In this embodiment, the air freshener comprises a casing that is formed of sections 25 and 26. Section 26 is fabricated from scent-absorbing cardboard. Section 25 is configured as a hard structure, such as plastic, wood, etc. Section 25 is formed into the same shape as cardboard section 26. In this embodiment, sections 25 and 26 have the shape of a chocolate bar. Section 25 has portion 25A that is sized and shaped to be inserted into a USB port of a computer or a computer peripheral device. A printed circuit board 23 is connected to portion 25A. A portion of circuit board 23 is exposed so that it can electrically contact corresponding electrical contacts within a USB port of a computer or computer peripheral device. The remaining portion of printed circuit board 23 is located between casing sections 25 and 26. Heating element 24 is electrically connected to printed circuit board 23. Printed circuit board 23 and heating element 24 have the same structure as printed circuit board 19 and heating element 20, respectively, as shown in FIG. 20. Heating element 24 generates heat when electrical power is applied to it. In a preferred embodiment, heating element 24 is a resistor. In one embodiment, cardboard section 26 is glued to section 25. When portion 25A of section 25 is plugged into a USB port, electrical power is applied to the printed circuit board 23 which provides electrical power to heating element 24. As a result, heating element 24 generates heat which causes cardboard section 26 to emit a scent or fragrance. Cardboard section 26 can be configured to have any one of a variety of scents or fragrances, including perfumes, herbs, fruit, flowers, etc. In one embodiment, the fragrance or scent is applied to the cardboard by printing, including offset printing, block printing, and screen printing. These printing techniques are known in the art.

Referring to FIGS. 25 and 28, there is shown an air freshener in accordance with another embodiment of the present invention. In a preferred embodiment, this air freshener is disposable. In this embodiment, the air freshener comprises a casing that is formed of sections 29 and 30. Section 30 is fabricated from scent-absorbing cardboard. Section 29 is configured as a hard structure, such as plastic, wood, etc. Section 29 is formed into the same shape as cardboard section 30. In this embodiment, sections 29 and 30 have the shape of a hamburger. In one embodiment, cardboard section 30 is glued to section 29. Section 29 has portion 29A that is sized and shaped to be inserted into a USB port of a computer or a computer peripheral device. A printed circuit board 27 is connected to portion 29A. A portion of printed circuit board 27 is exposed so that it can electrically contact corresponding electrical contacts within a USB port. The remaining portion of printed circuit board 27 is located between casing sections 29 and 30. Printed circuit board 27 is substantially identical in construction to printed circuit board 19 (see FIG. 20). Heating element 28 is electrically connected to printed circuit board 27 and has the same configuration as heating element 20 shown in FIG. 20. Thus, in a preferred embodiment, this heating element is a resistor. Heating element 28 generates heat when electrical power is applied to it. When portion 29A of casing section 29 is inserted into a USB port, electrical power is applied to printed circuit board 27 which, in turn, provides electrical power to heating element 28. The electrical power applied to heating element 28 causes heating element 28 to generate heat which causes the scented cardboard section 30 to emit a scent or fragrance. The cardboard section 30 can be configured to have any one of a variety of scents or fragrances, including perfumes, herbs, fruit, flowers, etc. In one embodiment, the fragrance or scent is applied to the cardboard by printing, including offset printing, block printing, and screen printing. These printing techniques are known in the art.

Referring to FIGS. 29-32, there is shown air freshener 50 in accordance with a further embodiment of the present invention. In a preferred embodiment, air freshener 50 is disposable. Air freshener 50 comprises casing 52 that is formed of cardboard and has sections 54 and 56. Cardboard sections 54 and 56 are configured as scent-absorbing cardboard. In this embodiment, sections 54 and 56 have a generally circular shape. Sections 54 and 56 have through-holes 58 and 60, respectively, which are sized to receive a chain or key ring. Air freshener 50 comprises USB connector structure 70 that comprises portion 72 that is inserted into a USB port of a computer or computer peripheral device. Portion 72 comprises printed circuit 74 that electrically contacts corresponding circuits in the USB port of a computer or computer peripheral device. USB connector structure 70 further comprises heater element 76 and memory circuit 78. Heating element 76 and memory circuit 78 are electrically connected to printed circuit 74. Memory circuit 78 can store data that is received from the computer or computer peripheral device. Thus, in this embodiment, disposable air freshener 50 also functions as flash memory drive. Heating element 76 can be configured as any suitable electronic component that can generate heat when electrical power is applied to it. In one embodiment, heating element 76 is a resistor. Casing section 56 has a cut-out 80 that has a shape that conforms to the shape of USB connector structure 70. Thus, USB connector structure 70 fits into cut-out 80. As a result of this configuration, USB connector structure 70 is firmly and neatly sandwiched between casing sections 54 and 56. In one embodiment, sections 54 and 56 are laminated into a single structure. When portion 72 of USB connector structure 70 is plugged into a USB port of a computer or peripheral device, electrical power is applied to printed circuit 74 and to heating element 76. In response, heating element 76 generates heat that causes the scent-absorbing cardboard sections 54 and 56 to emit a scent or fragrance. The cardboard sections 54 and 56 can be configured to have any one of a variety of scents or aromas including perfumes, herbs, fruit, flowers, etc. In one embodiment, the fragrance or scent is applied to the cardboard by printing, including offset printing, block printing, and screen printing. These printing techniques are known in the art.

The principles, preferred embodiments and modes of operation of the present invention have been described in the foregoing specification. This invention should not be construed as limited to the particular forms disclosed, as these are to be regarded as illustrative rather than restrictive. Variations and changes may be made by those skilled in the art without departing from the spirit of the invention. Accordingly, the foregoing detailed description should be considered as exemplary in nature and not as limiting the scope and spirit of the invention as set forth in the attached claims.

The invention claimed is:

1. A disposable air freshener configured to be plugged into a USB port comprising:
   a casing comprising a plurality of layered sections, the plurality of layered sections comprising a pair of outer, scented cardboard sections and an inner, scented cardboard section between the pair of outer scented cardboard sections;
   a USB connector structure having a portion within the casing and a printed circuit portion extending from the casing, the printed circuit portion being configured to be plugged into a USB port; and
   a heat generating component electrically connected to the printed circuit portion, the heat generating component generating heat when electrical power is applied thereto whereby the heat causes the scent to be emitted by the scent-absorbing cardboard.

2. The disposable air freshener as claimed in claim 1 wherein the inner scented cardboard section has a cut-out region shaped to receive the portion of the USB connector structure that is within the casing.

3. The disposable air freshener as claimed in claim 1 wherein the plurality of layered sections are laminated.

4. The disposable air freshener as claimed in claim 1 further comprising a memory device electrically connected to the printed circuit portion of the USB connector structure.

5. The disposable air freshener as claimed in claim 1 wherein the casing has the shape of a pine tree.

6. The disposable air freshener as claimed in claim 1 wherein the casing has the shape of a chocolate bar.

7. The disposable air freshener as claimed in claim 1 wherein the casing has the shape of a hamburger.

8. The disposable air freshener as claimed in claim 1 wherein the casing has a generally circular shape.

9. The disposable air freshener as claimed in claim 1 wherein the casing has a predetermined shape that matches the shape of a consumer object.

10. A disposable air freshener configured to be plugged into a USB port comprising:
   a casing comprising a plurality of laminated layered sections, at least one section thereof being configured as scent-absorbing cardboard;
   a USB connector structure having a portion within the casing and a printed circuit portion extending from the casing, the printed circuit portion being configured to be plugged into a USB port; and
   a heat generating component electrically connected to the printed circuit portion, the heat generating component generating heat when electrical power is applied thereto whereby the heat causes the scent to be emitted by the scent-absorbing cardboard.

11. A disposable air freshener configured to be plugged into a USB port comprising:
   a casing comprising a plurality of laminated layered sections, at least one section thereof being configured as scent-absorbing cardboard;
   a USB connector structure having a portion within the casing and a printed circuit portion extending from the casing, the printed circuit portion being configured to be plugged into a USB port;
   a heat generating component electrically connected to the printed circuit portion, the heat generating component generating heat when electrical power is applied thereto whereby the heat causes the scent to be emitted by the scent-absorbing cardboard; and
   a memory device electrically connected to the printed circuit portion of the USB connector structure.

12. A disposable air freshener configured to be plugged into a USB port comprising:
   a casing comprising a plurality of laminated layered sections wherein at least one section is configured as scent-absorbing cardboard and at least one section is configured as a rigid non-cardboard structure;
   a USB connector structure having a portion within the casing and a printed circuit portion extending from the casing, the printed circuit portion being configured to be plugged into a USB port; and
   a heat generating component electrically connected to the printed circuit portion, the heat generating component generating heat when electrical power is applied thereto whereby the heat causes the scent to be emitted by the scent-absorbing cardboard.

13. The disposable air freshener as claimed in claim 12 wherein the rigid, non-cardboard structure is fabricated from plastic.

14. The disposable air freshener as claimed in claim 12 wherein the rigid, non-cardboard structure has an extending portion to which is joined to the printed circuit portion.

* * * * *